United States Patent
Von Krosigk et al.

(10) Patent No.: US 7,250,136 B2
(45) Date of Patent: *Jul. 31, 2007

(54) METHOD FOR CONTROLLING SPORE PRODUCING FUNGI AND BACTERIA

(76) Inventors: James Richard Von Krosigk, 2625 Cowey Rd., Nixon, TX (US) 78140; Thomas E. Peterson, 1143 Rennie Dr., Katy, TX (US) 77450

(*) Notice: Subject to any disclaimer, the term of this patent is extended or adjusted under 35 U.S.C. 154(b) by 476 days.

This patent is subject to a terminal disclaimer.

(21) Appl. No.: 10/408,595

(22) Filed: Apr. 7, 2003

(65) Prior Publication Data

US 2004/0042929 A1    Mar. 4, 2004

Related U.S. Application Data

(60) Provisional application No. 60/372,935, filed on Apr. 16, 2002.

(51) Int. Cl.
*A61L 2/00* (2006.01)

(52) U.S. Cl. ............... 422/28; 422/1; 424/404; 514/367; 514/558

(58) Field of Classification Search ............ 422/1, 422/28; 424/404; 514/367, 558
See application file for complete search history.

(56) References Cited

U.S. PATENT DOCUMENTS

| 5,604,250 A * | 2/1997 | Oppong et al. ............ 514/367 |
| 6,821,637 B1 * | 11/2004 | Von Krosigk et al. ... 428/537.7 |
| 2004/0261961 A1 * | 12/2004 | Aitta et al. ................ 162/76 |

* cited by examiner

*Primary Examiner*—Krisanne Jastrzab
(74) *Attorney, Agent, or Firm*—Buskop Law Group, PC; Wendy Buskop

(57) ABSTRACT

The invention is a method for controlling growth of spores of specific fungi to the vegetative state by introducing a salt of formic acid to an aqueous system forming a mixture, applying the mixture to a surface where fungal spore growth control is desired, and drying the surface with the mixture disposed thereon, thereby forming an ionic lattice on the surface that prevents fungal spore growth to a vegetative state.

30 Claims, No Drawings

METHOD FOR CONTROLLING SPORE PRODUCING FUNGI AND BACTERIA

The current application is a conversion of U.S. provisional application No. 60/372,935 filed on Apr. 16, 2002, and titled "COMPOSITION FOR TREATING TOXIC MOLD INFESTATION, AND METHODS OF APPLYING SAME".

FIELD OF THE INVENTION

The present invention relates to a method for controlling spore producing fungi and bacteria.

BACKGROUND OF THE INVENTION

The invention relates to an additive for the control of the growth of fungi and mold cells from their spore on the surfaces of objected treated with an aqueous systems. The invention was designed to control the growth by killing the vegetative growth of the fungi from its spore with an additive that can be blended into commercially available paints, spackle, adhesives, grout, and sealants used in the home and commercial construction industry. The additive can also be used in the paper making industry to control growth of fungi or mold during the making of paper that causes spoilage. The additive can also be used to control the growth of bacterial in automotive and air conditioning end uses by adding it to lubrication systems of cars, compressors for oil field drilling, transmission systems or cars and other motors, air conditioning and heating systems and the like.

An object of the invention is to provide an easy to use, environmentally friendly additive which is cheaper than those currently commercially available.

Another object of the invention is to provide an additive that is light and easy to transport additive. that does not adsorb water in a high humidity environment.

A final object of the invention is to provide and additive that does not cake or clog and can be easily flowed into a system in a continuous flow without the need to batch addition of the additive.

SUMMARY OF THE INVENTION

The invention relates to a method for controlling growth of spores of specific fungi to the vegetative state. The method entails introducing a salt of formic acid to an aqueous system forming a mixture, applying the mixture to a surface where fungal spore growth control is desired, and drying the surface with the mixture disposed thereon. The drying step forms an ionic lattice on the surface that prevents fungal spore growth to a vegetative state.

The invention relates to an additive which is contemplated to kill the spores of fungus which includes in particular certain *penicillium* species and certain *Stachybotrys* species

DETAILED DESCRIPTION

Before explaining the present invention in detail, it is to be understood that the invention is not limited to the particular embodiments and that it can be practiced or carried out in various ways.

The invention relates to an additive for use in various aqueous systems

Biological fouling due to the growth of fungi from spores after pretreatment to control the fungi is a serious economic problem in many commercial and industrial uses.

The growth of fungi and mold from spores after a surface has been treated has wreaked havoc in the home insurance industry, where families have to be moved out of their homes to treat the initial killing of the fungi growth, only to discover a year or two later that the fungi has grown back creating a serious health hazard.

Fungi known as *Strachybotrys* species, *penicillium* species and various *aspergillus* species create spores to propagate. Although numerous commercial additives exist to kill the vegetative growth of the fungi, typically these additives must be used in extremely high and toxic concentrations to destroy the spores of these fungi. The use of high concentrations of these known additives, when added to aqueous systems, destroys valuable intrinsic properties of the formulation to which they are added. For example, if bleach is used to kill vegetative fungus, and it is added in high concentration to a lubricant system of an air conditioner, typically, the polar characteristics of the lubricant fluid would be harmed. Also, other additives, when added in quantities large enough to additionally kill the spores, have resulted in clogged system, without the continued ability to flow freely.

A need has existed for an additive that can be easily flowed into a preexisting preferably aqueous system which does not destroy the underlying advantages of the aqueous system to which it is added which may include the fundamental chemical characteristics of that system.

The present invention addresses these needs.

The invention is a method for controlling growth of spores of specific fungi to the vegetative state. The method begins by introducing a salt of formic acid to an aqueous system forming a mixture.

The salt of formic acid introduced to the aqueous system can be a metal salt or an organic salt. Examples of metal salts include cesium formate, sodium formate, zinc formate, lithium formate, calcium formate, potassium diformate, potassium di-formate and combinations. Examples of organic salts include ammonium formate, ethyl formate, methyl formate, amine formate, butyl formate, propyl formate or combinations thereof. The composition can also include a salt of citric acid, oxalic acid, maleic acid, acetic acid, fumaric acid, humic acid, fulvic acid, malic acid, glutaric acid, or glutamic acid.

The aqueous systems contemplated in the method include paints, lubricants, cooling systems, liquid adhesives, air conditioning systems, and similar such systems. The aqueous system can also be a cooling water tower, an air cleaner, a swimming pool, a spa, an industrial water system, a laundry detergent, a bleaching agent, a recycling water system, an oil field water, a sweet water, a gas scrubber, or a water slide.

The method can also further comprise that step of adding a second salt of formic acid that differs from the salt of formic acid to the mixture.

The preferred embodiment of the method continues by applying the mixture to a surface where fungal growth from spore is not desired.

The surface is a porous surface, such as sheet rock, wood, rock, brick, concrete, a painted surface, foam, insulation, ceiling tiles, wall and floor tiles, and combinations.

The mixture can be applied to the surface in a thin coat using one of the following methods: spraying, dipping, wiping, sponging, brushing, rolling, waxing, or combinations. It is preferred that the thin coat be no greater than 1 mm in thickness. In an alternative embodiment, a second coat of the mixture is applied to the surface and then dried after the initial step of drying the surface.

An additional active kavalactone can also be added to the mixture prior to applying it to the surface. The method can also involve adding between a 1:1 molar ratio of the salt of formic acid to active the kavalactone and a 5:1 molar ratio of the salt of formic acid to active the kavalactone.

The preferred embodiment of the method ends by drying the surface with the mixture disposed thereon. The step of dying forms an ionic lattice on the surface that prevents fungal spore growth to a vegetative state. In the preferred embodiment, the mixture is allowed to dry between 1 hour and 24 hours.

In an alternative, the method can include the step of disposing the mixture in a carrier prior to introducing the mixture to the aqueous system. Examples of such carriers are water, heavy water, distilled water, de-ionized water, tap water, and combinations. Other examples of carriers include glycol, propylene glycol, butylenes glycol, ethylene glycol and combinations. The carrier can also be a mixture of water and glycol or a hydrocarbon.

The method can further comprise the step of adding between 0.5 wt % and 10 wt % of a surfactant to the mixture prior to applying the mixture to the surface. The between 3 wt % and 5 wt % of the surfactant can be added to the mixture prior to applying the mixture to the surface.

The method can also include a paste from the mixture prior to applying the mixture to the surface, wherein the paste comprises an encapsulation agent, like colloidal oatmeal, to encapsulate the spores.

The invention is for an additive which can be mixed into a batch aqueous system or through a continuous flow aqueous system.

The additive can be in dry power form or blended with an acceptable carrier to reduce the cost of the additive for a particular system.

The additive is contemplated to be added to the aqueous system in amount between 0.01 and 50 parts per million (ppm) based on the total weight of the aqueous system.

SALTS OF FORMIC ACID—The key ingredient is contemplated to be a salt of a formic acid, and in the preferred embodiment, the salt is a potassium formate. It is contemplated that a usable formulation to treat spore growth could contain between 0.1 and 70 wt % potassium formate, however, between about 0.1 wt % and 50 wt % potassium formate or similar salt of formic acid could be used.

In a second embodiment of the invention, a second salt of formic acid can be added to the first salt, wherein the first salt is potassium formate and the second salt is ceseium formate. The preferred ratio of the potassium formate to the cesium formate would be 5:1.

A formulation of potassium formate with cesium formate would utilize between 1 and 50 wt % of the cesium formate, more preferably between 1 and 5 wt % of the cesium formate when used in combination with another salt of formic acid, such as potassium formate.

The salts can be a metal salt, such as cesium formate, sodiumformate, zinc formate, lithium formate, calcium formate, potassium di-formate, potassium formate and combinations thereof.

The salts can be an organic salt, such as ammonium formate, ethyl formate, methyl formate, amine formate, butyl formate, propyl formate and combinations of these.

KAVALACTONES—In yet another embodiment of the invention, an amount of active kavalactone can be added to the additive comprising the first salt of formic acid, notably the potassium formate. The additional kavalactone can be added in amounts between 0.01 and 50 wt % of the overall additive formulation. A preferred embodiment contemplates using between 1-50 wt % of kavalactone based on the wt % of the total composition prior to addition to the aqueous system. Yet another embodiment contemplates using between 1-20 wt % of active kavalactone based on the total wt % of the composition prior to introduction to the aqueous system.

Kavalactone is known as piper methysticum. It is from the kava plant of the New Guinea Indonesia area. The extract of the kava root is known to contain a class of structurally related chemical compounds termed kavalactones. Kavalactones possess low bio-availability and are practically insoluble in water. The invention relates to the unexpected discovery that three kavalactones, diydrokawain, dihydromethysticin and kawain exhibit inhibitory effect on the growth of fungi spores. Although is known that kavalactones have exhibited inhibitory effects on cytokines such as interleukin-12, see U.S. patent application publication No. 20020187169 filed May 11, 2002, which is hereby incorporated by reference. The reference does not teach any use attributed to it in combination with a salt of formic acid to inhibit spore growth after treatment of the vegetative state of the same fungi.

SURFACTANTS—Additionally, this composition may include surfactants. A sulfamic acid can be used as a stabilizer. The molar ratio of surfactant to the salt of formic acid is contemplated to range from 1:30 to 1:60.

It is contemplated that between 0.5 and 10.0 wt %, preferably between 3 and 5 wt %, surfactants could be used in this invention.

Other components that could be used in addition to or as substitution for surfactants include components termed antioxidants, ultraviolet stabilizers, dyes and viscosifiers, and combinations of these.

A viscosifier usable in this invention would be xanthan gum, carboxymethyl cellulose, starch guargum and combinations of these.

CARRIERS—The formulation can be disposed in a carrier prior to introduction to an aqueous system.

The carrier is preferably water. Different types of water can be used, including heavy water, distilled water, deionized water, tap water and combinations thereof.

Other than water, glycol can be used as a carrier, such as propylene glycol, butylenes glycol, ethylene glycol and combinations of these.

The invention also contemplates that the carrier can be a mixture of water and glycol or a hydrocarbon.

Hydrocarbons which would be useful as carriers include mineral spirits, ethanol, butanol, propanol, naptha, and combinations thereof.

The invention contemplates that the spore growth controlling component can be spayed onto a surface, such as with a propellant. Typical propellants could be butane, propane, and inert gas such as nitrogen, carbon dioxide, air, and combinations of these.

If a propellant is used, it could comprise between 1 and 30% by volume of a desired container for spray on purposes.

Alternatively the formulation can be sponged on, brushed on, wiped on. Alternatively, components, such as wood or sheet rock could be soaked in the formulation or dredged in the formulation if a large vat full of the formulation was used.

AQUEOUS SYSTEM—The invention can be used with various aqueous systems such as paints, lubricants, transmission fluids, or air conditioning systems.

It is contemplated that is can be used with cooling water towers, air cleaners, swimming pools, spas, industrial water systems, laundry detergents, bleaching agents, recycling water systems, oil field water, sweet water, gas scrubbers, or even water slides.

SURFACES—The formulation can be disposed on any number of surfaces to control spore growth.

ENCAPSULATION AGENT—Colloidal oatmeal can be used as an ingredient to form a paste with the novel composition and provide a means to encapsulate the spores to insure controlled growth.

Typical colloid oatmeal is oat gel available from Quaker Oats.

The unique oatmeal contains L-histines to kill the vegetative growth. The killing of the vegetative growth is an unexpected result of combining the oatmeal with the salt of the formic acid.

A paste of the formulation could be created as follows (the powder is mixed at a shear rate):

a. 30 wt % of potassium formate;
b. 60 wt % of colloidal oatmeal; and
c. 10 wt % tap water.

The ingredients are blended and mixed for about 2 minutes then the paste is ready to be applied to the surface.

The invention also contemplates that the carrier can be a mixture of water and glycol or a hydrocarbon.

The fungi growth to which the invention can be applied includes *Stachybotrys parvispora, Stachybotrys chartarum, Stachybotyrs kampalensis, Stachybotrys theobromae, Stachybotrys bisbyi, Stachybotrys cylindrospora, Stachybotrys dichroa, Stachybotrys oenanthes* or *Stachybotrys nilagerica* and combinations thereof.

The invention can also treat the fungi growth of *Aspergillus fumigatus, Aspergillus flavus, Aspergillus oryzae, Aspergillus niger, Aspergillus niger, Aspergillus foetidus, Aspergillus phoenicus, Aspergillus nomius, Aspergillus ochraceus, Aspergillus ostianus, Aspergillus auricomus, Aspergillus parasiticus, Aspergillus sojae, Aspergillus restrictus, Aspergillus caesillus, Aspergillus conicus, Aspergillus sydowii, Aspergillus tamari, Aspergillus terreus, Aspergillus ustus, Aspergillus versicolor* and combinations thereof.

*Aspergillus terreus* can also be treated with the invention.

The invention can treat spores from the fungi growth of *Absidia corymbifera, Absidia coerulea, Absidia glauca* and combinations thereof.

The invention can treat the fungi growth and spores of *Cladosporium herbarum* and *Fusarium oxysporum*.

The invention is contemplated to control spores from fungi growth of *Acremonium strictum, Alternaria alternate, Apopphysomyces elegans, Saksena vasiformis* and combinations thereof.

The fungi growth of *Penicillium freii, Penicillium verrucosum, Penicillium hirsutum, Penicillium alberechii, Penicillum aurantiogriseum, Penicillium polonicum, Penicillium viridicatum, Penicillium hirsutum, Penicillium brevicompactum, Penicillium chrysogenum, Penicillium griseofulvum, Penicillium glandicola, Penicillium coprophilum, Penicillium crustosum, Penicillium citrinum, Penicillium sartoryi, Penicillium westlingi, Penicillium corylophilum, Penicillium decumbens, Penicillium echinulatum, Penicillium solitum, Penicillium camembertii, Penicillium commune, Penicillium echinulatum, Penicillium sclerotigenum, Penicillium italicum, Penicillium expansum, Penicillium fellutanum, Penicillium charlesii, Penicillium janthinellum, Penicillium raperi, Penicillium madriti, Penicillium ochrochloron, Penicillium spinulosum, Penicillium glabrum, Penicillum thomii, Penicillium pupurescens,* and combinations thereof are also contemplated as susceptible to treatment with this invention.

In order that the invention described herein may be more readily understood, the following examples are set forth. It should be understood that these examples are for illustrative purposes only and not to be construed as limiting this invention in any manner. All references cited herein are expressly incorporated by reference in their entirety.

EXAMPLE 1

ADDITIVE—50 wt % of potassium formate is mixed with grout mix to add to a sealing composition, such as Easy Grout, in a ratio of 90:10 of additive to sealing composition.

EXAMPLE 2

ADDITIVE—50 wt % of potassium formate is mixed with 5 wt % of cesium formate and 45 wt % of a carrier. The carrier is water and is added to a coating for sheet rock in a ratio of 93:7 of additive to sheet rock coating known as Gypsum Brand available from US Gypsum, Inc.

EXAMPLE 3

ADDITIVE—30 wt % of potassium formate is mixed with an active kavalactone, namely Kaua Kaua Extract. The formed mixture is then added to a carrier, such as water, and added to a paint formulation such as a Sherman William Latex-based paint.

EXAMPLE 4

ADDITIVE—30 wt % of potassium formate is mixed with 2.5 wt % of cesium formate and 30 wt % of an active kavalactone, namely dihydrokawain forming a mixture. The mixture is then added to a carrier, namely, water in an amount up to 37.5 wt % of the water and added to a swimming pool water system.

The following is a chart of the results of treatment on various fungi:

| Example | Strachybotrys % killed | Penicillium % killed | Asperg % killed |
| --- | --- | --- | --- |
| 1 | 100 | 99.9+ | 100 |
| 2 | 100 | 100 | 100 |
| 3 | 100 | 100 | 100 |
| 4 | 100 | 100 | 100 |

The method of the invention can be used to control *Bacillus anthracis, Brucella abortus, Brucella melitensis, Brucella suis, Burkholderia mallei* (formally called *Pseudomonas mallei*), *Burkholderia pseudomallei* (formally called *Pseudomonas pseudomallei*), and *Botulinum neurotoxin* producing species of *Clostridium*.

While this invention has been described with emphasis on the preferred embodiments, it should be understood that within the scope of the appended claims the invention might be practiced other than as specifically described herein.

What is claimed is:

1. A method for controlling growth of spores of specific fungi to the vegetative state comprising:
   a. introducing a salt of formic acid to an aqueous system forming a mixture;

b. adding a second salt of formic acid which differs from the salt of formic acid to the mixture;

c. applying the mixture to a surface where fungal spore growth control is desired; and d. drying the surface with the mixture disposed thereon, thereby forming an ionic lattice on the surface that prevents fungal spore growth to a vegetative state.

2. The method of claim 1, wherein the surface is a porous surface.

3. The method of claim 2, wherein the porous surface is sheet rock, wood, rock, brick, concrete, a painted surface, foam, insulation, ceiling tiles, wall and floor tiles, and combinations thereof.

4. The method of claim 1, wherein the mixture is applied in a thin coat less than one millimeter in thickness to the surface.

5. The method of claim 1, wherein the step of applying the mixture is by spraying, dipping, wiping, sponging, brushing, rolling, waxing or combinations thereof.

6. The method of claim 1, wherein after the step of drying the surface, a second coat of the mixture is applied to the surface and then dried.

7. The method of claim 1, wherein the salt of formic acid introduced to the aqueous system is a metal salt.

8. The method of claim 7, wherein the metal salt is cesium formate, sodium formate, zinc formate, lithium formate, calcium formate, potassium di-formate, potassium formate or combinations thereof.

9. The method of claim 1, wherein the salt of formic acid introduced to the aqueous system is an organic salt.

10. The method of claim 9, wherein the organic salt, is ammonium formate, ethyl formate, methyl formate, amine formate, butyl formate, propyl formate or combinations thereof.

11. The method of claim 1, further comprising the step of adding active kavalactone to the mixture prior to applying it to the surface.

12. The method of claim 11, further comprising the step of adding between a 1:1 molar ratio of the salt of formic acid to active kavalactone and a 5:1 molar ratio of the salt of formic acid to active kavalactone.

13. The method of claim 1, further comprising the step of disposing the mixture in a carrier prior to introducing the mixture to the aqueous system.

14. The method of claim 13, wherein the carrier is a water selected from the group consisting of heavy water, distilled water, de-ionized water, tap water, and combinations thereof.

15. The method of claim 13, wherein the carrier is a glycol selected from the group consisting of propylene glycol, butylenes glycol, ethylene glycol and combinations thereof.

16. The method of claim 13, wherein the carrier is a mixture of water and glycol or a hydrocarbon.

17. The method of claim 1, further comprising the step of adding between 0.5 wt % and 10 wt % of a surfactant to the mixture prior to applying the mixture to the surface.

18. The method of claim 17, wherein between 3 wt % and 5 wt % of the surfactant is added to the mixture prior to applying the mixture to the surface.

19. The method of claim 1, wherein the specific fungi is *Stachybotrys parvispora, Stachybotrys chartarum, Stachybotyrs kampalensis, Stachybotrys theobromae, Stachybotrys bisbyi, Stachybotrys cylindrospora, Stachybotrys dichroa, Stachybotrys oenanthes* or *Stachybotrys nilagerica* and combinations thereof.

20. The method of claim 1, wherein the specific fungi is *aspergillus fumigatus, aspergillus flavus, aspergillus oryzae, aspergillus niger, aspergillus foetidus, aspergillus phoenicus, aspergillus nomius, aspergillus ochraceus, aspergillus ostianus, aspergillus auricomus, aspergillus parasiticus, aspergillus sojae, aspergillus restrictus, aspergillus caesillus, aspergillus conicus, aspergillus sydowii, aspergillus tamari, aspergillus terreus, aspergillus ustus, aspergillus versicolor* and combinations thereof.

21. The method of claim 1, wherein the specific fungi is *absidia corymbifera, absidia coerulea, absidia glauca* and combinations thereof.

22. The method of claim 1, wherein the specific fungi is *acremonium strictum, alternaria alternate, apopphysomyces elegans, Saksena vasiformis* and combinations thereof.

23. The method of claim 1, wherein the specific fungi is *Penicillium freii, Penicillium verrucosum, Penicillium hirsutum, Penicillium alberechii, Penicillum aurantiogriseum, Penicillium polonicum, Penicillium viridicatum, Penicillium brevicompactum, Penicillium chrysogenum, Penicillium griseofulvum, Penicillium glandicola, Penicillium coprophilum, Penicillium crustosum, Penicillium citrinum, Penicillium sartoryi, Penicillium westlingi, Penicillium corylophilum, Penicillium decumbens, Penicillium echinulatum, Penicillium solitum, Penicillium camembertii, Penicillium commune, Penicillium echinulatum,_Penicillium sclerotigenum,_Penicillium italicum, Penicillium expansum, Penicillium fellutanum, Penicillium charlesii, Penicillium janthinellum, Penicillium raperi, Penicillium madriti, Penicillium ochrochloron, Penicillium spinulosum, Penicillium glabrum, Penicillum thomii, Penicillium pupurescens*, and combinations thereof.

24. The method of claim 1, wherein the aqueous system is a paint, a lubricant, a cooling system, an liquid adhesive, or air conditioning system.

25. The method of claim 1, wherein the aqueous system is a cooling water tower, an air cleaner, a swimming pool, a spa, an industrial water system, a laundry detergent, a bleaching agent, a recycling water system, an oil field water, a sweet water, a gas scrubber, or a water slide.

26. The method of claim 1, wherein the mixture is allowed to dry between 1 hour and 24 hours.

27. The method of claim 1, wherein the mixture is applied in a thin coat no greater than 1 mm in thickness.

28. The method of claim 1, further comprising forming a paste from the mixture prior to applying the mixture to the surface, wherein the paste comprises an encapsulation agent to encapsulate the spores.

29. The method of claim 28, wherein the encapsulation agent is colloidal oatmeal.

30. The method of claim 1, wherein the step of introducing the salt of formic acid to an aqueous system forming a mixture further comprises a salt of citric acid, oxylate acid, lauric acid, and lactic acid.

* * * * *